(12) United States Patent
Gadenne et al.

(10) Patent No.: US 10,530,261 B2
(45) Date of Patent: Jan. 7, 2020

(54) HIGH-PERFORMANCE DC/DC CONVERTER WITH RESONATOR SENSING

(71) Applicant: General Electric Company, Schenectady, NY (US)

(72) Inventors: Aurelien Gadenne, Ile de France (FR); Julien Bouhraoua, Ile de France (FR); Jean-Francois Larroux, Ile de France (FR)

(73) Assignee: General Electric Company, Schenectady, NY (US)

( * ) Notice: Subject to any disclaimer, the term of this patent is extended or adjusted under 35 U.S.C. 154(b) by 248 days.

(21) Appl. No.: 15/678,282

(22) Filed: Aug. 16, 2017

(65) Prior Publication Data

US 2019/0058404 A1 Feb. 21, 2019

(51) Int. Cl.
*H02M 3/335* (2006.01)
*G01R 19/165* (2006.01)
*H05G 1/32* (2006.01)
*H02M 3/337* (2006.01)
*H05G 1/12* (2006.01)
*A61B 6/00* (2006.01)
*H02M 1/00* (2006.01)

(52) U.S. Cl.
CPC ........... *H02M 3/33569* (2013.01); *A61B 6/56* (2013.01); *G01R 19/16538* (2013.01); *H02M 3/3376* (2013.01); *H05G 1/12* (2013.01); *H05G 1/32* (2013.01); *H02M 2001/0009* (2013.01); *H02M 2001/0058* (2013.01)

(58) Field of Classification Search
CPC ............ H02M 3/33569; H02M 3/3376; G01R 19/16538; A61B 6/56; H05G 1/12
See application file for complete search history.

(56) References Cited

U.S. PATENT DOCUMENTS

| | | | | |
|---|---|---|---|---|
| 5,267,138 A * | 11/1993 | Shores | ................ | H02M 3/3376 363/132 |
| 5,341,278 A * | 8/1994 | Brooks | ................. | H02M 3/158 323/271 |
| 6,711,533 B1 | 3/2004 | Aymard et al. | | |
| 2003/0151929 A1* | 8/2003 | Figueroa | ........... | H02M 3/33507 363/21.01 |
| 2005/0073861 A1* | 4/2005 | Ke | .......... | H02M 1/34 363/20 |
| 2014/0092634 A1* | 4/2014 | Yan | .................... | H02M 3/33507 363/17 |
| 2014/0111016 A1* | 4/2014 | He | ........................ | H02M 3/285 307/82 |
| 2017/0366099 A1* | 12/2017 | Li | ..................... | H02M 3/33592 |

* cited by examiner

*Primary Examiner* — David P Porta
*Assistant Examiner* — Jeremy S Valentiner
(74) *Attorney, Agent, or Firm* — Boyle Fredrickson, S.C.

(57) ABSTRACT

In the present invention, a high-voltage DC/DC converter suitable for powering x-ray tubes and the like provides control of a voltage applied to a resonant circuit at least in part according to a timing of a monitored voltage on the resonator thereby compensating for variations in the parameter stability of the resonant circuit, nonlinearity in the resonant gain curve and frequency dependencies.

19 Claims, 4 Drawing Sheets

HIGH-PERFORMANCE DC/DC CONVERTER WITH RESONATOR SENSING

BACKGROUND OF INVENTION

The invention relates generally to high-powered DC power supplies suitable for x-ray tubes and similar high-voltage applications and in particular to a resonant circuit power supply having reduced sensitivity to parameter variations and the like.

Modern x-ray systems use an x-ray tube that accelerate electrons against a target to produce x-rays for therapeutic or imaging purposes. For this purpose, a high-voltage (e.g., 30-150 kilovolts) DC voltage is applied between a tube cathode and anode to provide the necessary electron acceleration. The power supply must be capable of producing current flows at kilowatt power levels.

The spectral content and influence of x-rays depends on the voltage and current applied to the x-ray tube and for this reason it is important that these values be stable.

High-voltage DC/DC (direct current to direct current) converters may be used to convert commonly available line voltage (after rectification and filtering) into the necessary high voltages for these applications. Such DC/DC converters first generate a lower voltage input DC bus by rectification and filtering of a convenient AC line voltage. This bus voltage is then switched by set of semiconductor devices to produce a synthesized AC signal that can be stepped-up in voltage using a transformer. Output from the transformer is then rectified to produce the necessary high voltage direct current. The intermediary steps of synthesizing an AC signal using the semiconductor devices allow feedback control of the output signal by varying a switching sequence of the semiconductor devices according to the output voltage when compared to desired command voltage. For example, the switching sequence of the semiconductor devices can be changed in duty cycle.

Improved efficiency of such DC/DC converters may be obtained through the use of a so-called "resonant converter" design. In such a design, the semiconductor devices produce a synthesized AC signal that is applied to a tank circuit (for example, a series resonant inductor and capacitor) to excite that tank circuit in the oscillation. The resulting AC waveform output from the tank circuit is closely sinusoidal providing improved conversion by the subsequent step-up transformer into a higher voltage AC signal and improved filtration of that higher voltage AC signal.

Despite advances in the resonant DC/DC convertor design, it can be difficult to provide precise voltage control in such designs because of the instability of the parameters of the resonant tank circuit which change over time and nonlinearities in the resonant gain curve of the resonant circuit.

BRIEF DESCRIPTION OF THE INVENTION

The present invention provides a hypo resonant DC to DC converter exhibiting improved stability through measurement of the voltage and current on the resonant tank circuit in real time and using that real-time information to directly control the switching of the semiconductors in producing the synthesized AC signal. By monitoring the timing of the signal on the resonant tank circuit, changes in the parameters of the resonant tank circuit are better accommodated, and improved control may be obtained during varying operating conditions despite nonlinearities and the like. Generally, in the hypo resonant converter, the switching frequency of the semiconductors will be below the resonant frequency of the resonant tank circuit.

Specifically, then, in one embodiment, the present invention provides a DC/DC converter circuit having a resonant circuit and a switch array receiving a source of DC voltage and operating according to a timing signal controlling the switches to provide alternating polarities of voltage to the resonant circuit. An output filter receives a voltage from the resonant circuit to provide a filtered direct current voltage output. A controller circuit receiving a desired voltage input signal and a voltage and current measurement of the resonant circuit operates to open and close switches of the switch array according to the values of the current voltage and current measurements to control the filtered direct current voltage output.

It is thus a feature of at least one embodiment of the invention to provide improved stability in a resonant circuit DC/DC converter by monitoring the resonant circuit directly in the control loop.

The controller circuit may compare values of the voltage and current measurement to predetermined threshold values to provide a timing of the opening and closing of switches of the switch array.

It is thus a feature of at least one embodiment of the invention to provide a simple method of extracting timing signals for controlling of the switch array from the voltage and current measurements on the resonator.

At least one predetermined threshold value maybe adjusted according to the desired voltage input signal.

It is thus a feature of at least one embodiment of the invention to integrate the timing signals generated by the resonant circuit with a control loop allowing control of the output of the DC/DC converter.

The predetermined threshold value against which the current measurement is measured is a zero current level.

It is thus a feature of at least one embodiment of the invention to provide a measurement of current polarity change in the resonant circuit presenting an opportunity for low loss switching.

The switch array may provide for four states of: (1) applying a positive voltage to the resonant circuit; (2) disconnecting from the resonant circuit immediately after state (1); (3) applying a negative voltage to the resonant circuit and; (4) disconnecting from the resonant circuit immediately after state (3); and the controller circuit may transition between state (4) and state (1), and between state (2) and (3) based on the voltage of the resonator with respect to a predetermined threshold voltage.

It is thus a feature of at least one embodiment of the invention to provide a simple state machine control of the switches of the switch array.

The controller circuit may transition between state (4) and state (1) when the voltage on the resonator rises above a predetermined negative threshold voltage and may transition between states (2) and (3) when the voltage on the resonator drops below a predetermined positive voltage threshold.

It is thus a feature of at least one embodiment of the invention to provide a simple method of generating timing signals from the voltage on the resonant circuit.

The controller circuit may transition between state (1) and state (2) when the current on the resonator rises crosses a zero current level in a downward direction and may transition between states (3) and (4) when the current on the resonator drops rises above a zero current level in an upward direction.

It is thus a feature of at least one embodiment of the invention to provide a simple method of generating off signals timed with zero current points.

The controller circuit may further include at least one of a proportional/integral control circuit and feedforward control circuit, the proportional/integral control circuit controlling the switch array according to the desired voltage input signal, and the filtered direct current output and the feedforward control circuit controlling the switch array according to the desired voltage input signal and a desired power output.

It is thus a feature of at least one embodiment of the invention to provide the benefits of standard control techniques in controlling the voltage output according to a command signal.

The output of the proportional/integral control circuit and the feedforward control circuit may be combined to adjust the predetermined threshold value against which the values of voltage measurements are compared.

It is thus a feature of at least one embodiment of the invention to provide a simple method of integrating the timing generating circuit of the present invention with standard control methodologies.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings.

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
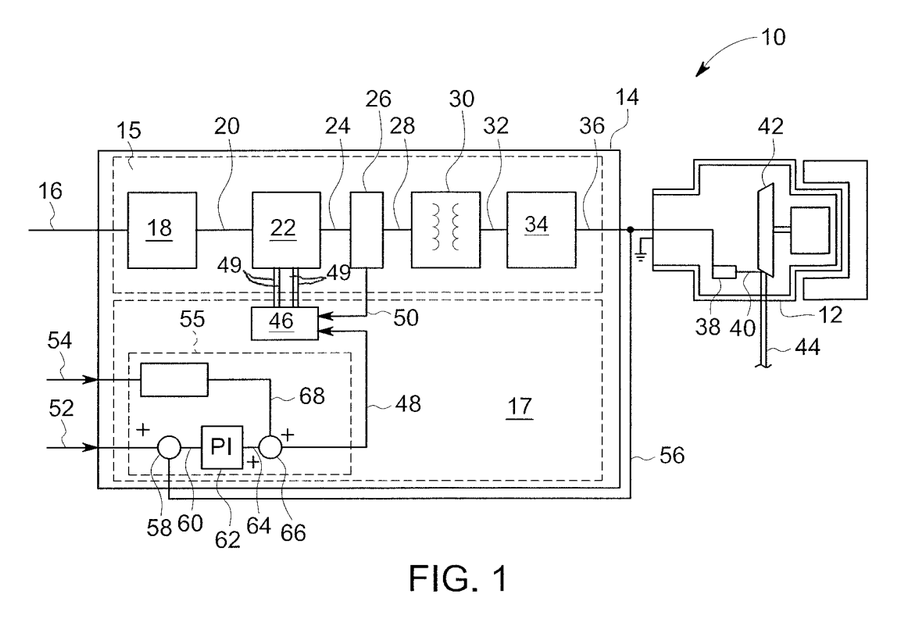
FIG. 1 is a block diagram of a high-voltage x-ray power supply constructed according to the present invention providing a power hardware block including a resonant tank circuit receiving a synthesized waveform from a switch array and a control block using measured current and voltage signals from the resonant tank circuit and feedback signals comparing an output voltage to a desired command voltage to control the switch array.

FIG. 1 illustrates one exemplary embodiment of an x-ray tube/power supply assembly 10 including an x-ray tube 12 communicating with a high-voltage DC power supply 14. Generally, the high-voltage DC power supply 14 includes a high-power section 15 and a low-power section 17.

The high-power section 15 of the power supply 14 will receive line voltage 16, for example, 100-240 volts AC at 50-60 hertz which may be converted by a rectifier/filter assembly 18 into desired DC bus voltage 20 suitable for semiconductor switching. This DC bus voltage 20 is received by a switch array 22 which converts the DC bus voltage 20 into a "square wave" drive signal 24 that feeds a resonant tank circuit 26, for example, formed from a series connected inductor. An output of the resonant tank circuit 26 provides a low-harmonic synthesized AC signal 28 that may be received by a step up transformer 30 providing a high-voltage AC signal 32. The high-voltage AC signal 32 is provided to an output rectifier/filter assembly 34 outputting a high-voltage DC output 36 suitable for providing voltage to a cathode assembly 38 of the x-ray tube 12 accelerating electron beam 40 toward a target 42 to produce a beam of x-rays 44.

The high-power section 15 communicates with the low-power section 17 which, for example, may be implemented as a field programmable gate array (FPGA) microprocessor or the like. The low-power section 17 provides a switch sequence generator 46 generating control signals over control lines 49 to control the switch array 22. In this regard, the switch sequence generator 46 may receive a feedback control signal 48 and resonant circuit voltage and current signals 50 from the resonant tank circuit 26 to control the switching of the switches of the switch array 22 through switch control lines 49 as will be discussed below.

The feedback control signal 48 may, for example, be generated from a feedback controller 55 receiving voltage command signal 52 (indicating a desired operating voltage of the x-ray tube 12) and an output power signal 54 (designating a desired maximum output power limit) each provided by the associated x-ray equipment (for example, CT machine, x-ray machine, or the like) according to methods known in the art. In one embodiment, the voltage command signal 52 is compared to a feedback signal 56 (equal to the high-voltage DC output 36) at summing junction 58 to produce an error signal 60 representing the difference between these values. The error signal 60 may be received by a proportional/integral controller 62 of a type known in the art to provide a first correction signal 64. This first correction signal 64 may then be received by summing junction 66 which also receives a feedforward signal 68 generated from as a function of the feedback signal 56 and voltage command signal 52. Feedback controllers 55 of this type are generally understood in the art and may be tuned and/or modified according to techniques understood with respect feedback control.

The feedback control signal 48, as will be described in greater detail below, will be used to adjust the switching of the semiconductors of the switch array 22 to raise or lower the voltage of the high-voltage DC output 36 to conform with the voltage command signal 52.

Figure 2:
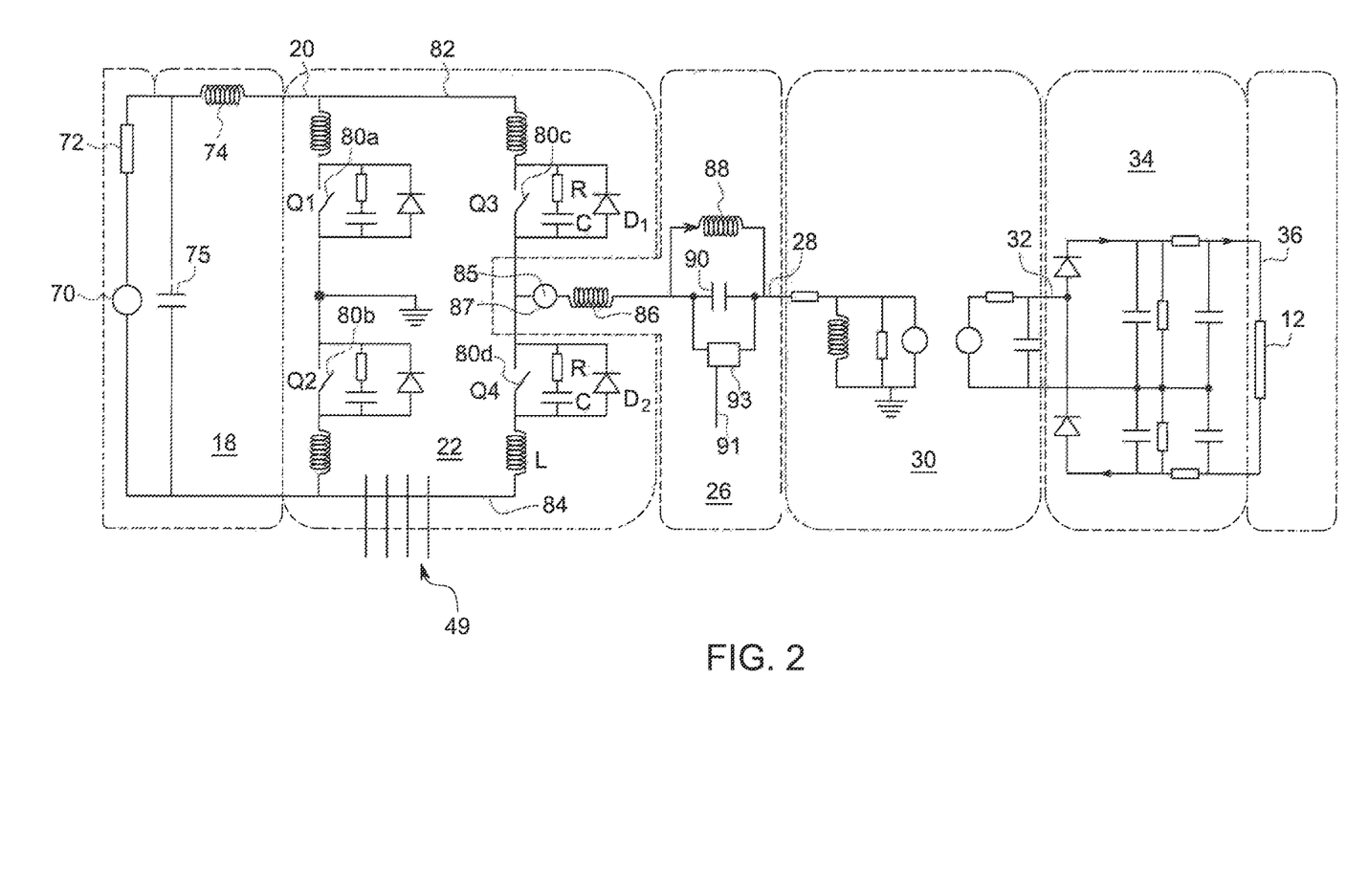
FIG. 2 is a simplified schematic representation of the power hardware block of FIG. 1 including the switch array providing power to the resonant tank circuit.

FIG. 2 provides a functional block diagram for the various elements discussed above. In this functional block diagram, the components are represented using standard lumped element representations for simplicity and clarity. In this regard, the rectifier/filter assembly provides a DC source 70 having an effective series resistance 72, for example, providing a lump sum representation of the source impedance and voltage of rectified line power. A low pass filter formed from series inductor 74 and parallel capacitor 75 provides a smooth DC power-to-feed switch array 22.

The switch array 22 may employ a standard H bridge having four solid-state switches 80a-80d (also referred to as switches Q1-Q4, respectively) whose state as either "on" (conducting) or "off" (nonconducting) may be controlled by the switch sequence generator 46 through control lines 49. For example, the control lines 49 may lead to the bases or gates of semiconductor devices used to implement switches 80. Standard bypass diode snubber circuitry and inrush control circuitry may be associated with each switch 80a as will be generally understood in the art.

Within the switch array 22, a first switch 80a will controllably connect a positive bus voltage rail 82 (received from the rectifier/filter assembly 18) to ground. A corresponding switch 80b will operate to connect a negative bus voltage rail 84 (also received from the rectifier/filter assembly 18) to ground. Similarly switch 80c will operate to connect the positive bus voltage rail 82 to the drive signal 24 and switch 80d will operate to connect the drive signal 24 to the negative voltage rail 84.

In operation only one of each pair of switches 80a and 80b and pair of switches 80c and 80d will be on at one time to prevent short-circuits between the bus rails 82 and 84. It will be recognized, however, that proper sequencing of the switches can generate a positive- and negative-going square wave to be received by the resonant tank circuit 26.

The resonant tank circuit 26 may provide for an inductor 86 connected in series to a capacitor 90, these two components forming a series resonant circuit having a resonant frequency determined by the values of these components. An optional parallel-configured inductor 88 may be provided in parallel to capacitor 90. An end of the inductor 86 not connected to the capacitor 90 receives the drive signal 24. The end of the capacitor 90 not connected to the inductor 86 provides the synthesized AC signal 28 output to the transformer 30.

A current signal 87, being the current-through-series inductor 86, may be measured by a current sensor 85, for example, a small resistive element, Hall effect device, current transformer, or the like. Likewise, a voltage signal 91 may be measured by a voltage sensor 93 connected across the capacitor 90, for example, a differential amplifier. The signals may be digitized by analog-to-digital conversion circuitry (not shown) to be processed by the low-power section 17 as will be discussed below.

As noted above, the transformer 30 may provide a step up of the synthesized AC signal 28 output from the resonant tank circuit 26 which provides the high-voltage AC signal 32 received by the rectifier/filter assembly 34. The rectifier/filter assembly 34 provides a half bridge rectifier and filter assembly producing the high-voltage DC output 36 received by the load represented by the x-ray tube 12.

Figure 3:
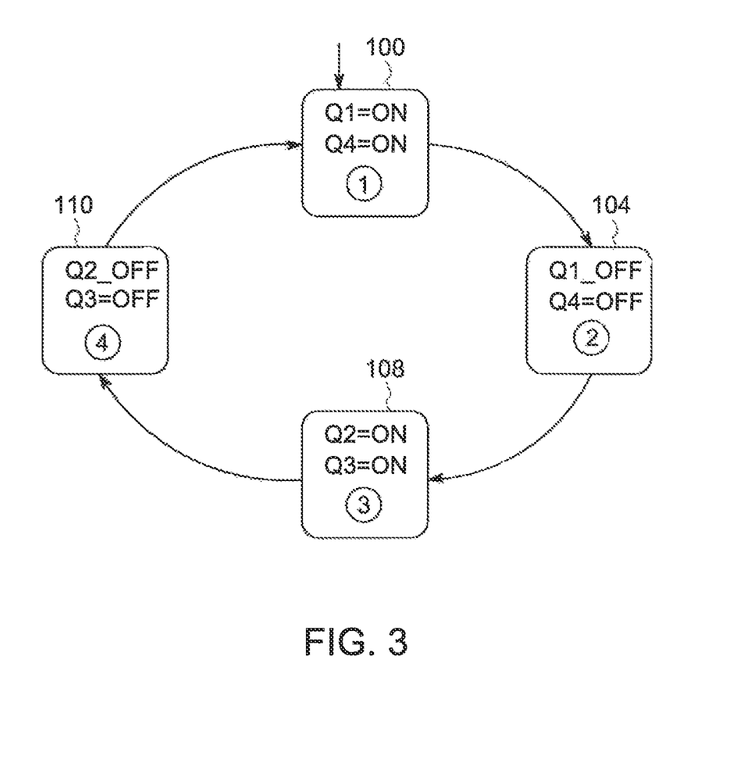
FIG. 3 is a state diagram showing transitions between four different switch states of the switch array.
Figure 4:
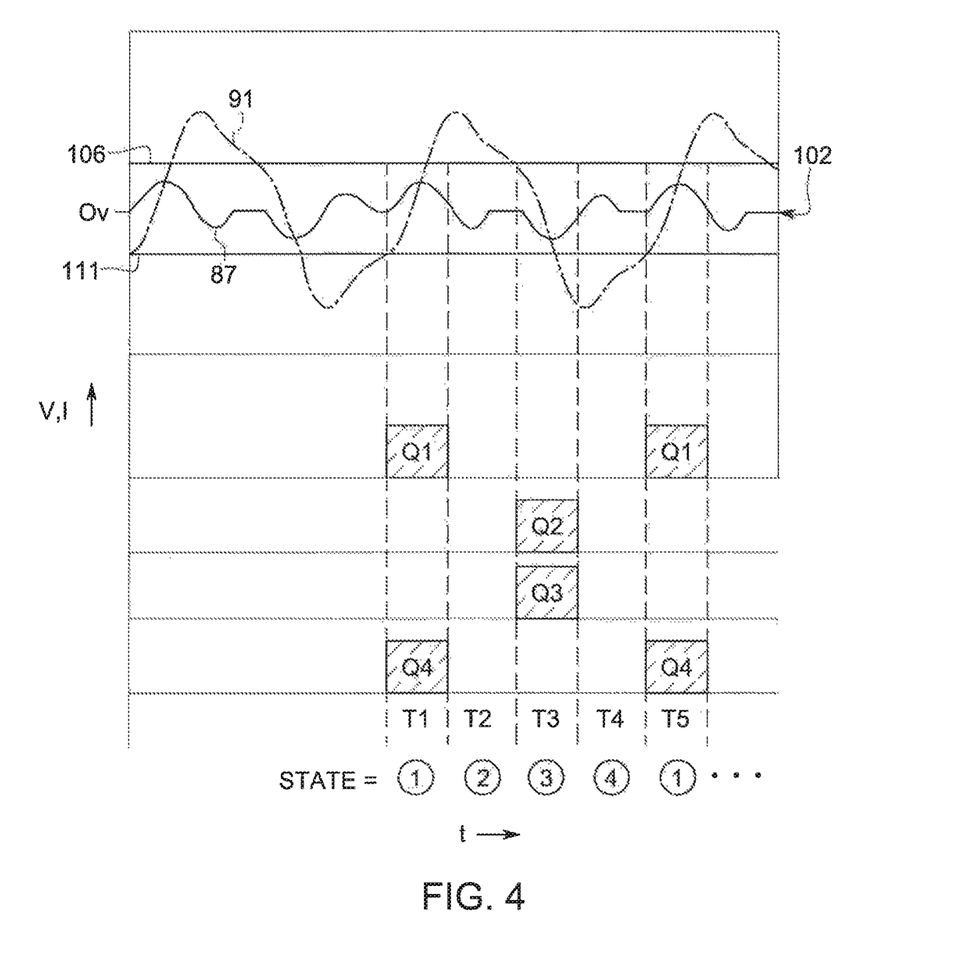
FIG. 4 is a plot of a measurement of voltage and current in the resonant tank circuit juxtaposed with a state diagram showing timing signals for control of the switch array as influenced by the measured voltage and current signals.

Referring now to FIGS. 3 and 4, the current signal 87 and voltage signal 91 may be used to control the switching of switches 80 by the signal switch control lines 49. In this regard, the switches 80 will generally move between four switch states shown in circled numbers: a first state 100 in which switches Q1 and Q4 are turned on, a second state 104 in which switches Q1 and Q4 are turned off and then off, a third state 108 in which switches Q2 and Q3 are turned on, and a fourth state 110 in which switches Q2 and Q3 are turned off. Each of these states will be associated with a particular set of activations of switch control lines 49 providing timing signals turning on particular ones of the switches Q1-Q4 by providing binary control signals as is understood in the art.

Starting at a state 100 shown in FIG. 3 and represented by time T1 in FIG. 4, transistors Q1 and Q4 may be turned on. This state 100 continues until the current signal 87 drops to cross a zero current level 102 upon which a state transition occurs from state 100 to state 104. At state 104, both transistors Q1 and Q4 are turned off by controlling their respective switch control lines 49 and as indicated by time T2. This state 104 continues until the voltage signal 91 crosses below a first positive voltage setpoint 106 (above zero voltage) whereupon a state transition to state 108 occurs with transistors Q2 and Q3 turned on as indicated at time T3. The state 108 continues until the current signal 87 rises through the zero current level 102 causing a state transition to state 110 were transistors Q2 and Q3 are turned off as indicated at time T4. This state 108 continues until the voltage signal 91 transitions above a second negative voltage setpoint 111 at which point the switch control lines 49 transition to state 100 again turning on transistors Q1 and Q4 as indicated at time T5. The cycling through the states 100, 104, 108, and 110 continues indefinitely while the power supply 14 operates.

Referring again to FIG. 1, the signals on the switch control lines 49 are also controlled by the signal 48 which adjusts the voltage levels of the positive voltage setpoint 106 and negative voltage setpoint 111 to control the voltage of the high-voltage DC output 36 while allowing precise timing to be determined by the current signal 87 and voltage signal 91.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A Direct Current-to-Direct Current (DC/DC) converter circuit comprising:
   a switch array having inputs adapted to receive a Direct Current (DC) voltage at an input of the switch array and operative according to a timing signal that controls switches in the switch array to provide a squarewave drive signal alternating between a first DC voltage and a second DC voltage at an output of the switch array, wherein a polarity of the first DC voltage is opposite a polarity of the second DC voltage;
   a resonant circuit configured to receive the squarewave drive signal, the resonant circuit having an inductor and a capacitor configured to operate in resonance and further configured to provide an Alternating Current (AC) voltage at an output of the resonant circuit;
   an output filter operative to receive the AC voltage from the resonant circuit and to provide a filtered DC voltage output; and
   a controller circuit having inputs adapted to receive a desired voltage input signal, a measured voltage across the capacitor of the resonant circuit; and a measured current through the inductor of the resonant circuit, and the controller circuit is configured to generate control signals to open the switches of the switch array according to values of the measured current through the inductor of the resonant circuit and to close the switches of the switch array according to values of the measured voltage across the capacitor of the resonant circuit to control the filtered DC voltage output.

2. The DC/DC converter circuit of claim 1 wherein the controller circuit compares values of the measured voltage across the capacitor of the resonant circuit and measured current through the inductor of the resonant circuit to predetermined threshold values to provide a timing of an opening and closing of the switches of the switch array.

3. The DC/DC converter circuit of claim 2 wherein one of the predetermined threshold values is adjusted according to the desired voltage input signal.

4. The DC/DC converter circuit of claim 3 wherein one of the predetermined threshold values is a zero-current level against which the measured current through the inductor of the resonant circuit is compared.

5. The DC/DC converter circuit of claim 2 wherein the controller circuit is further configured to generate the control, signals for the switch array to selectively operate in one of four states: (1) in a first state, the switch array is operative to connect the DC voltage to the resonant circuit, wherein the DC voltage is applied with a positive polarity, defining either the first DC voltage or the second DC voltage; (2) in a second state, the switch array is operative to disconnect the DC voltage from the resonant circuit immediately after state (1); (3) in a third state, the switch array is operative to connect the DC voltage to the resonant circuit, wherein the DC voltage is applied with a negative polarity, defining either the first DC voltage or the second DC voltage; and (4) in a fourth state, the switch array is operative to disconnect the DC voltage from the resonant circuit immediately after state (3), and wherein the controller circuit transitions between state (4) and state (1), and between state (2) and (3) based on the measured voltage across the capacitor of the resonant circuit with respect to a predetermined threshold voltage.

6. The DC/DC converter circuit of claim 5 wherein the controller circuit transitions between state (4) and state (1) when the measured voltage across the capacitor of the resonant circuit rises above a predetermined negative threshold voltage and transitions between states (2) and (3) when the measured voltage across the capacitor of the resonant circuit drops below a predetermined positive voltage threshold.

7. The DC/DC converter circuit of claim 5 wherein the controller circuit transitions between state (1) and state (2), and between state (3) and (4) based on the measured current through the inductor of the resonant circuit with respect to a zero-current level.

8. The DC/DC converter circuit of claim 7 wherein the controller circuit transitions between state (1) and state (2) when the measured current through the inductor of the resonant circuit crosses a zero-current level in a downward direction and transitions between states (3) and (4) when the measured current through the inductor of the resonant circuit rises above of a zero-current level in an upward direction.

9. The DC/DC converter circuit of claim 2 wherein the controller circuit further includes at least one of a proportional/integral control circuit and a feedforward control circuit, the proportional/integral control circuit controls the switch array according to the desired voltage input signal and the filtered DC voltage output and the feedforward control circuit controls the switch array according to a desired power output.

10. The DC/DC converter circuit of claim 9 wherein an output of the proportional/integral control circuit and an output of the feedforward control circuit are combined to adjust the predetermined threshold value.

11. The DC/DC converter circuit of claim 1 wherein the controller circuit is implemented using a field programmable gate array including an analog-to-digital converter operating at a conversion speed in excess of 15 megahertz.

12. The DC/DC converter circuit of claim 1 further including:
a DC power supply providing the DC voltage;
a transformer positioned between the resonant circuit and the output filter; and
wherein the output filter includes a rectifier and filter capacitors for converting an AC signal to a DC signal;
wherein the switch array provides a bridge of electrically controllable semiconductors.

13. The DC/DC converter circuit of claim 1 wherein the resonant circuit is a series-connected inductor and capacitor with the switch array connecting to one of the inductor and capacitor and the output filter connecting to an other of the inductor and capacitor.

14. An x-ray system comprising:
an x-ray tube receiving a voltage and producing x-rays;
a power supply connected to the x-ray tube to provide the voltage, the power supply including:
a switch array having inputs adapted to receive a Direct Current (DC) voltage at an input of the switch array and operative according to a timing signal that controls switches in the switch array to provide a squarewave drive signal alternating between a first DC voltage and a second DC voltage at an output of the switch array, wherein a polarity of the first DC voltage is opposite a polarity of the second DC voltage;
a resonant circuit configured to receive the squarewave drive signal, the resonant circuit having an inductor and a capacitor configured to operate in resonance and further configured to provide an Alternating Current (AC) voltage at an output of the resonant circuit,
an output filter operative to receive the AC voltage from the resonant circuit and to provide a filtered DC voltage output, wherein the filtered DC voltage output is the voltage the power supply provides to the x-ray tube; and
a controller circuit having inputs adapted to receive a desired voltage input signal, the filtered DC voltage output, a measured voltage across the capacitor of the resonant circuit, and a measured current through the inductor of the resonant circuit, and operative to close the switches of the switch array according to values of the measured voltage across the capacitor of the resonant circuit and to open the switches of the switch array according to values of the measured current through the inductor of the resonant circuit to control the filtered DC voltage output to match the desired voltage input signal.

15. The x-ray system of claim 14 wherein the controller circuit compares values of the measured voltage across the capacitor of the resonant circuit and measured current through the inductor of the resonant circuit to predetermined threshold values to provide a timing of an opening and closing of the switches of the switch array.

16. The x-ray system of claim 15 wherein at least one of the predetermined threshold values is adjusted according to the desired voltage input signal.

17. The x-ray system of claim 16 wherein the predetermined threshold value against which the measured current through the inductor of the resonant circuit is a zero-current level.

18. A method of controlling a Direct Current-to-Direct Current (DC/DC) converter of a type having:
- a switch array receiving a source of Direct Current (DC) voltage and operating according to a timing signal controlling switches in the switch array to provide a squarewave drive signal alternating between a first DC voltage and a second D voltage at an output of the switch array, wherein a polarity of the first DC voltage is opposite a polarity of the second DC voltage;
- a resonant circuit configured to receive the squarewave drive signal, the resonant circuit having an inductor and a capacitor configured to operate in resonance and further configured to provide an Alternating Current (AC) voltage at an output of the resonant circuit; and
- an output filter receiving the AC voltage from the resonant circuit to provide a filtered DC voltage output; the method comprising the steps of:
  (a) receiving a desired voltage input signal; and
  (b) monitoring the desired voltage input signal, the filtered DC voltage output, a measured voltage across the capacitor of the resonant circuit, and a measured current through the inductor of the resonant circuit to open the switches of the switch array according to values of the measured current through the inductor of the resonant circuit and to close the switches of the switch array according to values of the measured voltage across the capacitor of the resonant circuit to control the filtered DC voltage output.

19. The method of claim 18 wherein the control of the filtered DC voltage output compares values of the measured voltage across the capacitor of the resonant circuit and measured current through the inductor of the resonant circuit to predetermined threshold values to provide a timing of the opening and closing of switches of the switch array.

* * * * *

UNITED STATES PATENT AND TRADEMARK OFFICE
CERTIFICATE OF CORRECTION

PATENT NO. : 10,530,261 B2
APPLICATION NO. : 15/678282
DATED : January 7, 2020
INVENTOR(S) : Aurelien Gadenne et al.

Page 1 of 1

It is certified that error appears in the above-identified patent and that said Letters Patent is hereby corrected as shown below:

In the Claims

Claim 1, Column 6, Line 65, delete ";" and substitute therefor -- , --;

Claim 5, Column 7, Line 22, after "trol" delete ",";

Claim 10, Column 8, Line 4, delete "valve" and substitute therefor -- valves --;

Claim 18, Column 9, Line 14, delete "D" and substitute therefor -- DC --.

Signed and Sealed this
Sixteenth Day of June, 2020

Andrei Iancu
*Director of the United States Patent and Trademark Office*